(12) United States Patent
Hancock et al.

(10) Patent No.: US 12,295,653 B2
(45) Date of Patent: May 13, 2025

(54) ELECTROSURGICAL INSTRUMENT

(71) Applicant: CREO MEDICAL LIMITED, Chepstow Wales (GB)

(72) Inventors: Christopher Paul Hancock, Bath (GB); George Ullrich, Bangor (GB); Steve Morris, Chepstow (GB); David Webb, Bangor (GB); Shaun Preston, Chepstow (GB); Leif Geoghegan, Chepstow (GB); Dan Crocker, Chepstow (GB); Sandra Swain, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 1085 days.

(21) Appl. No.: 17/280,135

(22) PCT Filed: Oct. 1, 2019

(86) PCT No.: PCT/EP2019/076567
§ 371 (c)(1),
(2) Date: Mar. 25, 2021

(87) PCT Pub. No.: WO2020/070113
PCT Pub. Date: Apr. 9, 2020

(65) Prior Publication Data
US 2021/0338326 A1    Nov. 4, 2021

(30) Foreign Application Priority Data
Oct. 3, 2018   (GB) ..................................... 1816128

(51) Int. Cl.
*A61B 18/18*    (2006.01)
*A61B 18/12*    (2006.01)
(Continued)

(52) U.S. Cl.
CPC ...... *A61B 18/1815* (2013.01); *A61B 18/1206* (2013.01); *A61B 18/1477* (2013.01);
(Continued)

(58) Field of Classification Search
CPC . A61B 18/18; A61B 18/1815; A61B 18/1206; A61B 18/042; A61B 18/1492;
(Continued)

(56) References Cited

U.S. PATENT DOCUMENTS 6,347,251 B1   2/2002  Deng
6,770,070 B1   8/2004  Balbierz
(Continued)

FOREIGN PATENT DOCUMENTS

CN     104427951 A    3/2015
EP       1768596 A1   4/2007
(Continued)

OTHER PUBLICATIONS

International Preliminary Report on Patentability issued by the International Searching Authority corresponding to International Patent Application No. PCT/EP2019/076567, dated Dec. 2, 2020.
(Continued)

*Primary Examiner* — Thomas A Giuliani
(74) *Attorney, Agent, or Firm* — ArentFox Schiff LLP

(57) ABSTRACT

In one aspect, the disclosure presents an electrosurgical instrument for performing haemostasis by radiating microwave energy from a distal tip, where conductive radiating electrodes are coated in an insulating non-stick material. In another aspect, the disclosure provides an electrosurgical instrument for performing haemostasis using radiofrequency or microwave electromagnetic energy, where a distal tip of the instrument comprises a conductive hollow needle for conveying fluid to or from a treatment site, wherein the hollow needle is electrically grounded.

22 Claims, 8 Drawing Sheets

(51) Int. Cl.
*A61B 18/14* (2006.01)
*A61B 18/00* (2006.01)
(52) U.S. Cl.
CPC ............... *A61B 2018/00011* (2013.01); *A61B 2018/00077* (2013.01); *A61B 2018/00083* (2013.01); *A61B 2018/0013* (2013.01); *A61B 2018/00178* (2013.01); *A61B 2018/00589* (2013.01); *A61B 2018/1823* (2013.01); *A61B 2018/1869* (2013.01); *A61B 2218/002* (2013.01)
(58) Field of Classification Search
CPC .... A61B 2018/1869; A61B 2018/1876; A61B 2018/1884; A61B 2018/1892; A61B 2018/00029; A61B 2018/00607; A61B 2018/00958; A61B 2018/1861; A61B 2018/00994; A61B 2018/00011; A61B 2018/00178; A61B 2018/1823; A61B 2018/00196; A61B 2018/00577; A61B 2018/1273; A61B 2018/1475; A61B 2018/1838; A61B 2218/002; A61B 2218/007; A61B 2218/001
USPC ...... 606/33, 34, 37, 41, 42; 607/98, 99, 101, 607/104, 105, 115, 116, 156
See application file for complete search history.

(56) References Cited

U.S. PATENT DOCUMENTS

| | | | | |
|---|---|---|---|---|
| 9,636,176 | B2* | 5/2017 | Hancock | A61B 18/1815 |
| 10,251,697 | B2* | 4/2019 | Hancock | A61B 18/1815 |
| 10,820,937 | B2* | 11/2020 | Hancock | A61B 18/1477 |
| 11,246,657 | B2* | 2/2022 | Hancock | A61B 18/042 |
| 2004/0059328 | A1 | 3/2004 | Daniel et al. | |
| 2011/0238055 | A1 | 9/2011 | Kim et al. | |
| 2013/0289557 | A1* | 10/2013 | Hancock | H01Q 13/08 606/33 |
| 2014/0042154 | A1 | 2/2014 | Cronin | |
| 2016/0120588 | A1* | 5/2016 | Amoah | A61B 18/1206 606/39 |

FOREIGN PATENT DOCUMENTS

| | | |
|---|---|---|
| GB | 2545179 A | 6/2017 |
| GB | 2547941 A | 9/2017 |
| JP | 2015521873 A | 8/2015 |
| JP | 2017500958 A | 1/2017 |
| WO | WO 2017/103209 A1 | 6/2017 |
| WO | WO 2018/202758 A1 | 11/2018 |

OTHER PUBLICATIONS

International Search Report and the Written Opinion issued by the International Searching Authority corresponding to International Patent Application No. PCT/EP2019/076567, dated Feb. 4, 2020.
Search Report under Section 17(5) issued by the British Patent Office corresponding to British Application No. GB1816128.1 dated Mar. 19, 2019.

* cited by examiner

ELECTROSURGICAL INSTRUMENT

CROSS-REFERENCE TO RELATED APPLICATIONS

This application is a National Stage entry of International Application No. PCT/EP2019/076567, filed on Oct. 1, 2019, which claims priority to British Patent Application No. 1816128.1, filed on Oct. 3, 2018. The disclosures of the priority applications are hereby incorporated in their entirety by reference.

FIELD OF THE INVENTION

The invention relates to an electrosurgical instrument for delivering microwave energy and/or radiofrequency energy to biological tissue in order to ablate the target tissue. The electrosurgical instrument includes a fluid delivery channel coupled to a needle for delivering fluid to a treatment site. The probe may be inserted through a channel of an endoscope or catheter, or may be used in laparoscopic surgery or open surgery.

BACKGROUND TO THE INVENTION

Electromagnetic (EM) energy, and in particular microwave and radiofrequency (RF) energy, has been found to be useful in electrosurgical operations, for its ability to cut, coagulate, and ablate body tissue. Typically, apparatus for delivering EM energy to body tissue includes a generator comprising a source of EM energy, and an electrosurgical instrument connected to the generator, for delivering the energy to tissue. Conventional electrosurgical instruments are often designed to be inserted percutaneously into the patient's body. However, it can be difficult to locate the instrument percutaneously in the body, for example if the target site is in a moving lung or a thin walled section of the gastrointestinal (GI) tract. Other electrosurgical instruments can be delivered to a target site by a surgical scoping device (e.g. an endoscope) which can be run through channels in the body such as airways or the lumen of the oesophagus or colon. This allows for minimally invasive treatments, which can reduce the mortality rate of patients and reduce intraoperative and postoperative complication rates.

Tissue ablation using microwave EM energy is based on the fact that biological tissue is largely composed of water. Human soft organ tissue is typically between 70% and 80% water content. Water molecules have a permanent electric dipole moment, meaning that a charge imbalance exists across the molecule. This charge imbalance causes the molecules to move in response to the forces generated by application of a time varying electric field as the molecules rotate to align their electric dipole moment with the polarity of the applied field. At microwave frequencies, rapid molecular oscillations result in frictional heating and consequential dissipation of the field energy in the form of heat. This is known as dielectric heating.

This principle is harnessed in microwave ablation therapies, where water molecules in target tissue are rapidly heated by application of a localised electromagnetic field at microwave frequencies, resulting in tissue coagulation and cell death. It is known to use microwave emitting probes to treat various conditions in the lungs and other organs. For example, in the lungs, microwave radiation can be used to treat asthma and ablate tumours or lesions.

RF EM energy can be used for cutting and/or coagulation of biological tissue. The method of cutting using RF energy operates based on the principle that as an electric current passes through a tissue matrix (aided by the ionic contents of the cells, i.e. sodium and potassium), the impedance to the flow of electrons across the tissue generates heat. When a pure sine wave is applied to the tissue matrix, enough heat is generated within the cells to vaporise the water content of the tissue. There is thus a large rise in the internal pressure of the cell that cannot be controlled by the cell membrane, resulting in the cell rupturing. When this occurs over a wide area it can be seen that tissue has been transected.

RF coagulation operates by applying a less efficient waveform to the tissue, whereby instead of being vaporised, the cell contents are heated to around 65° C. This dries out the tissue by desiccation and also denatures the proteins in the walls of vessels and the collagen that makes up the cell wall. Denaturing the proteins acts as a stimulus to a coagulation cascade, so clotting is enhanced. At the same time, collagen in the cell wall is denatured from a rod like molecule to a coil, which causes the vessel to contract and reduce in size, giving the clot an anchor point, and a smaller area to plug.

Some electrosurgical instruments may be used with a fluid delivery system for delivering a fluid (e.g. liquid and/or gas) to a treatment site. In some cases, the fluid delivery system may be used to administer liquid medication to a treatment site. For example, it is known to administer adrenaline to the site of a bleed in order to constrict blood vessels during severe bleeds.

As another example, the fluid delivery system may be used to deliver argon gas to a treatment site, to perform argon plasma coagulation (APC). APC is a surgical technique for controlling bleeding in a manner that does not require physical contact between the electrosurgical instrument and the target tissue. In APC, a jet of argon is ionised with the microwave and/or RF energy delivered by the electrosurgical instrument, to cause coagulation and control bleeding.

SUMMARY OF THE INVENTION

The disclosure herein presents two aspects, which may be provided together or separately.

In a first aspect, the invention provides an electrosurgical instrument for performing haemostasis by radiating microwave energy from a distal tip, in which conductive electrodes from which the microwave energy is radiated are coated in an insulating non-stick material.

In a second aspect, the invention provides an electrosurgical instrument for performing haemostasis using radiofrequency (RF) or microwave electromagnetic (EM) energy, in which a distal tip of the instrument comprises a conductive hollow needle for conveying fluid to or from a treatment site, wherein the hollow needle is electrically grounded.

For the first aspect, the inventors have found that when tissue is coagulated or ablated, it may have a tendency to stick to the instrument tip. This may result in damage to the tissue or cause bleeding when the instrument tip is removed from the treatment site. Providing a non-stick coating over at least the conductive elements (e.g. electrodes) from which the microwave energy is radiated serves to prevent tissue from sticking to the instrument tip. In some examples, the whole instrument tip may be coated. Providing a non-stick coating may facilitate removal of the instrument tip from a treatment site following application of microwave energy. The non-stick coating may be made of a bio-compatible material, such as Parylene C or Parylene D.

The inventors have realised that haemostasis may be effectively performed using radiated microwave energy. When microwave energy is used, the non-stick coating may be insulating (i.e. non-conductive), as the microwave energy is radiated from the radiating structure. A variety of insulating bio-compatible non-stick materials are known and may be used for this purpose. In contrast, haemostasis is conventionally performed using RF energy. In this case, no insulating non-stick coating can be used, as the electrodes must be exposed to allow the RF current to flow into the target tissue. The inventors are not aware of any suitable material which is bio-compatible, conductive, and non-stick that could be used to provide a non-stick coating for a device that performs haemostasis by delivery energy by conduction. Thus, performing haemostasis with radiated microwave energy enables the instrument tip to be coated with insulating non-stick material, which may prevent tissue from sticking to the instrument tip and facilitate use of the instrument.

For the second aspect, the inventors have found that when the hollow needle is not grounded (e.g. when it is left floating), it may interfere with the microwave and/or RF energy emitted by the electrosurgical instrument. The inventors have found that the interference effects caused by a non-grounded hollow needle are particularly noticeable at microwave energies. This may cause the radiation profile of the electrosurgical instrument to be distorted, and/or the efficiency with which EM energy is delivered into target tissue to be reduced.

The inventors have found that by grounding the hollow needle, interference of the hollow needle with the microwave and/or RF energy emitted by the electrosurgical instrument may be reduced. This may serve to improve the shape of the radiation profile of the electrosurgical instrument, e.g. by preventing it from extending too far in front of the distal tip when the needle is extended. This may improve the efficiency with which EM energy is delivered into target tissue, e.g. by ensure that energy delivered is confined to the immediate vicinity of the distal tip. As a result, control of delivery of EM energy to target tissue may be improved.

According to the first aspect, there may be provided an electrosurgical instrument comprising: a coaxial feed cable for conveying microwave energy, the coaxial feed cable having an inner conductor, an outer conductor, and a dielectric material separating the inner conductor and the outer conductor; an instrument tip disposed at a distal end of the coaxial feed cable to receive the microwave energy and/or the radiofrequency energy; and a fluid channel for conveying fluid to the instrument tip, wherein the instrument tip comprises: a radiating structure for radiating the microwave energy into biological tissue; and a hollow needle in fluid communication with the fluid channel, the hollow needle being arranged to deliver fluid from the fluid channel to a treatment site, and wherein the radiating structure is coated with an insulating non-stick material.

The insulating non-stick material may be applied as a coating over all or part of the instrument tip. For example, the instrument tip may be coated with the insulating non-stick material, or the coating may be restricted to the radiating structure.

The coating of the insulating non-stick material may have a thickness equal to or less than 40 μm, e.g. in the range 1-40 μm. Preferably the thickness is equal to or less than 10 μm, e.g. in the range 3-4 μm. The thickness of the insulating material may vary over the insulating tip. It may have thinner portions disposed over the radiating structure.

The insulating non-stick material may be biocompatible. In some embodiments, the non-stick material is Parylene C or Parylene D.

According to the second aspect, there may be provided an electrosurgical instrument comprising: a coaxial feed cable for conveying microwave energy and/or radiofrequency energy, the coaxial feed cable having an inner conductor, an outer conductor, and a dielectric material separating the inner conductor and the outer conductor; an instrument tip disposed at a distal end of the coaxial feed cable to receive the microwave energy and/or the radiofrequency energy; and a fluid channel for conveying fluid to the instrument tip; wherein the instrument tip comprises: an energy delivery structure for delivering the microwave energy and/or the radiofrequency energy into biological tissue; and a hollow needle in fluid communication with the fluid channel, the hollow needle being arranged to deliver fluid from the fluid channel to a treatment site, wherein the energy delivery structure comprises a radiating structure for radiating the microwave energy into biological tissue, and wherein the hollow needle is electrically connected to the outer conductor to ground the hollow needle.

The first and second aspects may be combined, e.g. to provide an electrosurgical instrument with both a grounded needle and an insulating non-stick coating. Further optional features that are applicable to both aspects are set out below.

The instrument may operate to coagulate and/or ablate target tissue in the body. For example, the instrument may be used to treat tissue in the lungs or gastrointestinal tract, however it may be used to treat tissue in other organs (e.g. the uterus). In order to efficiently treat target tissue, the instrument tip may need to be located as close as possible (and in many cases inside) the target tissue. In order to reach the target tissue (e.g. in the lungs), the device may need to be guided through passageways (e.g. airways) and around obstacles. This means that the instrument will ideally be as flexible as possible and have a small cross section. Particularly, the device should be very flexible near its tip, where it may need to be steered along narrow passageways such as bronchioles which can be narrow and winding.

The coaxial feed cable may be a conventional low loss coaxial cable that is connectable at one end to an electrosurgical generator. In particular, the inner conductor may be an elongate conductor extending along a longitudinal axis of the coaxial feed cable. The dielectric material may be disposed around the inner conductor, e.g. the first dielectric material may have a channel through which the inner conductor extends. The outer conductor may be a sleeve made of conductive material that is disposed on the surface of the dielectric material. The coaxial feed cable may further include an outer protective sheath for insulating and protecting the cable. In some examples, the protective sheath may be made of or coated with a non-stick material to prevent tissue from sticking to the cable.

The fluid channel may serve to convey fluid (e.g. liquid or gas) from a proximal end of the electrosurgical instrument to the instrument tip. The fluid channel may be connectable at its proximal end to a fluid supply. For example, the fluid channel may be used to convey liquid medication (e.g. adrenaline) to the instrument tip. Where the electrosurgical instrument is used to perform APC, the fluid channel may be used to convey argon gas to the instrument tip. The fluid channel may also be used to transport fluid from the instrument tip to the proximal end of the electrosurgical instrument. For example, fluid present in a treatment site around the instrument tip may be aspirated through the hollow needle and evacuated via the fluid channel, in order to evacuate the fluid from the treatment site. The fluid channel may comprise a flexible tube (lumen) which extends along a length of the electrosurgical instrument, e.g. from the proximal end of the electrosurgical instrument to the instrument tip.

In some examples, the fluid channel may run alongside the coaxial feed cable. The fluid channel and the coaxial feed cable may be housed within a flexible instrument sleeve, e.g. the instrument sleeve may define a lumen which carries the coaxial feed cable and the fluid channel. The instrument sleeve may be made of, or coated with a non-stick material (e.g. PTFE), to prevent tissue from sticking to it. An insert may be provided in the instrument sleeve, to maintain the position of the coaxial feed cable and fluid channel within the instrument sleeve. Alternatively the instrument sleeve may be a multi-lumen tube, such that the coaxial feed cable is received within a first lumen of the instrument sleeve, and the fluid channel is received within a second lumen of the instrument sleeve.

In some examples, the fluid channel may be housed within the coaxial feed cable. For example, the dielectric material in the coaxial feed cable may include a lumen through which the fluid channel extends. In another example, the inner conductor may be a hollow conductor, e.g. the inner conductor may be formed by a tube of conductive material. In this case, the fluid channel may be provided within the hollow inner conductor. Housing the fluid channel within the coaxial feed cable may serve to reduce an outer diameter of the electrosurgical instrument.

The instrument tip is located at the distal end of the coaxial feed cable, and serves to deliver EM energy conveyed along the coaxial feed cable into target tissue. The instrument tip also serves to deliver fluid from the fluid channel to a treatment site. The fluid channel may terminate near the distal end of the coaxial feed channel, e.g. before the instrument tip. Alternatively, a portion of the fluid channel may extend into the instrument tip. The instrument tip may be permanently or removably attached to the coaxial feed cable and the fluid channel.

The energy delivery structure is arranged to deliver the microwave and/or RF energy conveyed by the coaxial feed cable. The radiating structure is electrically connected to the coaxial feed cable to receive the microwave energy. The radiating structure may be configured for microwave energy having a predetermined energy, in order to cause the instrument to produce a desired radiation profile and/or type of treatment (e.g. tissue ablation, cutting or coagulation). For example, the radiating structure may be configured as a monopolar microwave antenna, e.g. the radiating structure may include an elongate conductor which is connected to the inner conductor and arranged to radiate microwave energy along its length. Alternatively, the radiating structure may be configured as a bipolar microwave antenna, e.g. the radiating structure may include a pair of electrodes that are respectively connected to the inner conductor and the outer conductor, and that are arranged to radiate microwave energy.

Where the energy delivery structure is designed to deliver RF energy, the energy delivery structure may include a pair of RF electrodes that are respectively connected to the inner conductor and the outer conductor. The pair of RF electrodes may act as an active electrode and a return electrode, such that tissue located in a region between the electrodes is ablated or coagulated by the RF energy.

Where the electrosurgical instrument is used to perform APC, the energy delivery structure may include a pair of electrodes that are disposed in the vicinity of the hollow needle, in order to spark and sustain a plasma from the argon gas using the microwave and/or RF energy.

In some cases, the energy delivery structure may be designed to deliver both microwave and RF energy, either simultaneously or sequentially. For example, where the energy delivery structure includes a pair of electrodes, the pair of electrodes may act as active and return electrodes at RF frequencies, and they may act as a bipolar antenna at microwave frequencies.

The hollow needle serves to deliver fluid from the fluid channel to a treatment site. The treatment site may comprise a region of target biological tissue located in the vicinity of (e.g. in front of) the instrument tip. The hollow needle may be formed of a length of tube. The hollow needle may be made of a conductive material (e.g. metal). The hollow needle may have a proximal end, which is in fluid communication with the fluid channel, so that fluid from the fluid channel may be conveyed into the hollow needle. For example, the proximal end of the hollow needle may be located inside a distal portion of the fluid channel. A seal may be formed between the hollow needle and the fluid channel, to prevent fluid from leaking at the junction between the fluid channel and the hollow needle. The hollow needle may have a distal end having an opening, through which fluid may be dispensed into the treatment site. Fluid may also be aspirated into the needle through the opening in its distal end, to evacuate fluid from the treatment site. The distal end of the hollow needle may be sharp (e.g. pointed), to facilitate insertion of the hollow needle into tissue. For example, the hollow needle may be a hypodermic needle.

The hollow needle is electrically connected to the outer conductor of the coaxial feed cable. This serves to ground the hollow needle to the outer conductor. Typically, the outer conductor of the coaxial feed cable may be connected to electrical ground (e.g. 0 V), so both the outer conductor and the hollow needle may be grounded. The hollow needle may be electrically connected to the outer conductor using any suitable means. For example, a conductive wire or other conductor may be connected between the outer conductor and the hollow needle.

Because the hollow needle is electrically connected to the outer conductor, the hollow needle is not at a floating voltage relative to the coaxial feed cable. The electrical connection between the hollow needle and the outer conductor may also reduce any floating capacitance between the outer conductor and the hollow needle. As a result, interference effects caused by the hollow needle on the delivery of EM energy by the energy delivery structure may be reduced. This may be particularly beneficial for delivery of microwave energy, as the inventors have found that interference effects caused by the hollow needle may be more pronounced at microwave frequencies. Reducing interference effects of the hollow needle may serve to improve the radiation profile of the instrument tip (e.g. by reducing distortions caused by interference), as well as improve efficiency of EM energy delivery to target tissue. Grounding the hollow needle to the outer conductor may also improve the safety of the electrosurgical instrument, as this may prevent a large voltage from arising between hollow needle and the energy delivery structure.

In some embodiments, the instrument tip may comprise a grounding element arranged to electrically connect the hollow needle to the outer conductor. The electrical connection between the outer conductor and hollow needle may therefore be located in the instrument tip itself. The grounding element may electrically connect the hollow needle to a distal portion of the outer conductor. In some cases, the distal portion of the outer conductor may extend into the instrument tip. The grounding element may comprise a piece of conductive material that electrically connects the hollow conductor to the outer conductor. The grounding element may be connected to the hollow needle and outer conductor using any suitable means, e.g. via a mechanical connection, conductive adhesive (e.g. epoxy), or solder or weld joins. By providing the grounding element directly in the instrument tip, the length of the electrical path between the hollow needle and the outer conductor may be reduced. This may ensure a good electrical connection between the hollow needle and the outer conductor, and facilitate forming of the electrical connection.

In some embodiments, the grounding element may include a body having a first connection surface and a second connection surface arranged to retain the hollow needle and outer conductor respectively. The first connection surface and the second connection surface may be electrically connected together, e.g. as different surface areas of a common conductive body. The hollow needle may be electrically connected to the first connection surface. The outer conductor may be electrically connected to the second connection surface. As the hollow needle and outer conductor are both connected to surfaces on the body of the grounding element, the grounding element may serve to fix a position of the hollow needle relative to the outer conductor (and thus the coaxial feed cable). Thus, the grounding element may serve the dual function of electrically connecting the hollow needle to the outer conductor, and holding the hollow needle and outer conductor in place relative to one another. This may serve to improve the integrity of the instrument tip. The body of the grounding element may be a unitary component made of a conductive material (e.g. metal), in which case the hollow needle and outer conductor are electrically connected via the body of the grounding element. Alternatively, the body may be made of an insulating material, and first and second connection surfaces may be formed by conductive layers provided on surfaces of the body. An electrical path between the first and second connection surfaces may then be provided on or in the body.

The hollow needle may be electrically connected to the first connection surface using any suitable means. In one example, the hollow needle may be held against the first connection surface to form an electrical contact therebetween. Alternatively, the hollow needle may be attached to the first connection surface, e.g. using a conductive adhesive, or via a soldered or welded connection. The outer conductor may be electrically connected to the second connection surface in a similar fashion.

A shape of the first connection surface may be complementary to a shape of the hollow needle. This may improve the electrical connection between the first connection surface and the hollow needle. This may also serve to hold the hollow needle in place, to prevent unwanted movement of the hollow needle. For example, where the hollow needle has a circular cross-section, the first connection surface may be a rounded surface having a radius of curvature that matches a radius of the hollow-needle's cross-section. Similarly, a shape of the second connection surface may be complementary to a shape of the outer conductor.

In some embodiments the body of the grounding element may have a first channel extending therethrough, the first connection surface being formed in the first channel. The grounding element may have a generally cylindrical or conical shape, e.g. where the first channel is a centrally disposed aperture in which a portion of the hollow needle may be received. The first channel may extend through the body in a longitudinal direction, i.e. in a direction parallel to the longitudinal axis of the inner conductor. The first channel may be an open channel, e.g. it may constitute a groove in which a portion of the hollow needle is received. Alternatively, the first channel may be a closed channel, e.g. it may define a lumen in which a portion of the hollow needle is contained. The first channel may serve to hold the hollow needle in place in the grounding element. This may ensure that electrical connection between the hollow needle and the first connection surface is maintained. The first channel may also serve to restrict lateral movement of the hollow needle, e.g. movement in a direction perpendicular to the longitudinal direction. The first connection surface may be provided on a surface of the first channel, e.g. the first connection surface may be on a wall of the channel. Where the body of the grounding element is made of a conductive material, a wall of the first channel may provide the first connection surface. A shape of the first channel may be complementary to a shape of the hollow needle.

Where the hollow needle is movable relative to the instrument tip, the first channel may serve to provide a slidable electrical connection between the hollow needle and the grounding element. The hollow needle may thus be slidable relative to the outer conductor, and an electrical connection between the hollow needle and outer conductor may pass across a sliding interface. The first channel may also act to guide the hollow needle when it is moved relative to the tip.

In some embodiments, the first channel may include a flared portion located at a proximal end of the first channel, the flared portion having a cross-sectional area that increases towards the proximal end of the first channel. The flared portion may serve to guide or "funnel" the hollow needle into the first channel.

In some embodiments, the body of the grounding element may include a second channel extending therethrough, the second connection surface being formed in the second channel; and a distal portion of the outer conductor may be received in the second channel. The second channel may extend through the body in the longitudinal direction. The second channel may be parallel to the first channel. The second channel may be an open channel, e.g. it may constitute a groove in which the distal portion of the outer conductor is received. Alternatively, the second channel may be a closed channel, e.g. it may define a lumen in which the distal portion of the outer conductor is contained. The second channel may serve to hold the outer conductor in place in the grounding element. This may ensure that electrical connection between the outer conductor and the second connection surface is maintained. The second connection surface may be provided on a surface of the second channel, e.g. the first connection surface may be on a wall of the channel. Where the body of the grounding element is made of a conductive material, a wall of the second channel may provide the second connection surface. A shape of the second channel may be complementary to a shape of the hollow needle. The distal portion of the outer conductor may be a portion of the outer conductor located at or near a distal end of the coaxial feed cable. The distal portion of the outer conductor may extend into the instrument tip.

The body of the grounding element may include a proximal portion that is attached to a distal portion of the coaxial feed cable. The proximal portion of the body of the grounding element may serve to anchor the grounding element to the coaxial feed cable. This may serve to strengthen an interface between the coaxial feed cable and the instrument tip. This configuration may also serve to hold the hollow needle in place relative to the coaxial feed cable. The distal portion of the coaxial feed cable may be held in the proximal portion of the body via any suitable means. For example, the proximal portion of the body may include a channel in which the distal portion of the coaxial feed cable is received and held. The body of the grounding element may further include a distal portion, the first and second connection surfaces being located in the distal portion. The body of the grounding element may straddle an interface between the coaxial feed cable and the instrument tip, with the proximal portion of the body being located at the distal end of the coaxial feed cable, and the distal portion of the bod being located in the instrument tip. The grounding element may thus serve to improve the integrity of the electrosurgical instrument, as well as reduce interference caused by the hollow needle.

In some embodiments, the electrosurgical instrument may further comprise a first insulating sleeve arranged at a proximal end of the grounding element to guide the hollow needle into contact with the first connection surface. The first insulating sleeve may be made of a flexible insulating material (e.g. polyimide tube). The first insulating sleeve may serve to protect and insulate the hollow needle from its surroundings. The first insulating sleeve may define a passageway through which the hollow needle extends, and which guides the hollow needle into contact with the first connection surface. The first insulating sleeve may extend from the proximal end of the grounding element, in the longitudinal direction towards a proximal end of the instrument. In this manner, the first insulating sleeve may serve to align the hollow needle along the longitudinal direction. The first insulating sleeve may be particularly beneficial where the hollow needle is movable, as it may act to guide movement of the hollow needle in the longitudinal direction.

In some embodiments, the electrosurgical instrument may further comprise a second insulating sleeve arranged at a distal end of the grounding element to insulate the hollow needle from the radiating structure. The second insulating sleeve may be made of a flexible insulating material (e.g. polyimide tube). The second insulating sleeve may serve to insulate the hollow needle from the radiating structure and other components in the instrument tip. The second insulating sleeve may define a passageway through which the hollow needle extends. The second insulating sleeve may guide the hollow needle from the distal end of the grounding element towards a distal end of the instrument tip. For example, the second insulating sleeve may extend from the distal end of the grounding element to the distal end of the instrument tip.

In some cases, the first and second insulating sleeves may form a continuous insulating sleeve, the continuous insulating sleeve having an aperture through which the hollow needle is electrically connected to the first connection surface.

Where the electrosurgical instrument includes both the first insulating sleeve and the second insulating sleeve, the first insulating sleeve may have a larger cross-section than the second insulating sleeve. This may facilitate insertion of the hollow needle into the first insulating sleeve, in order to bring the hollow needle in electrical contact with the grounding element. In this manner, the larger first insulating sleeve may act to "funnel" the hollow needle towards the grounding element and the first connection surface. Using a larger diameter first insulating sleeve may also reduce drag on the hollow needle when it is moved relative to the instrument tip. This may facilitate moving the hollow needle relative to the instrument tip.

The cross section of the second insulating sleeve may approximately match a cross-section of the hollow needle. In this manner, the second insulating sleeve may ensure correct positioning of the hollow needle within the instrument tip.

In some embodiments, the hollow needle may be movable relative to the instrument tip between: a retracted position, in which a distal end of the hollow needle is set back from a distal end of instrument tip; and an exposed position, in which the distal end of the hollow needle protrudes beyond the distal end of the instrument tip. In this manner, when the hollow needle is not in use, it may be placed in the retracted position, to prevent accidentally damaging tissue. The needle may be moved to the exposed position when it is desired to deliver fluid to the treatment site, e.g. to administer medication to the treatment site. The hollow needle may be movable relative to the instrument tip in the longitudinal direction. When the hollow needle is in the retracted position, the distal end of the hollow needle may be located inside the instrument tip. The instrument tip may include a channel along which the hollow needle is movable, such that when the hollow needle is in the retracted position, the distal end of the hollow needle is located inside the channel.

The hollow needle may be movable relative to the instrument tip via any suitable mechanism. In some embodiments, the hollow needle may be movable by actuating (e.g. pushing or pulling) a control wire that is attached to the hollow needle. The control wire may be located inside the fluid channel, such that the control wire is attached to the hollow needle inside the fluid channel. Alternatively, the control wire may run alongside the fluid channel.

The electrical connection between the hollow needle and the outer conductor may be configured to allow movement of the hollow needle relative to the instrument tip. In this manner, the hollow needle may remain electrically connected to the outer conductor regardless of whether it is in the retracted position or the exposed position. For example, the electrical connection between the hollow needle and the outer conductor may be a slidable electrical connection. Where the grounding element includes a body having a first connection surface, the hollow needle may be slidable relative to the first connection surface. In some cases, it may be possible to fully withdraw the hollow needle from the instrument, tip such that it is no longer electrically connected to the outer conductor.

Where the grounding element includes a first channel, the first channel may be dimensioned to allow the hollow needle to slide longitudinally along the channel, whilst ensuring that the hollow needle remains in contact with the first connection surface.

The connection between the hollow needle and the fluid channel may be configured to allow movement of the hollow needle relative to the fluid channel. In this manner, when the hollow needle is moved relative to the instrument tip, the hollow needle may remain in fluid communication with the fluid channel. For example, where a proximal end of the hollow needle is located inside the fluid channel, the proximal end of the hollow needle may be movable along a length of the fluid channel. A sliding seal may be formed between hollow needle and the fluid channel, to enable movement of the hollow needle relative to the fluid channel whilst preventing fluid from escaping at the junction between the hollow needle and the fluid channel.

In some embodiments, the instrument tip may include an opening at a distal end thereof, such that, when the hollow needle is in the retracted position, the distal end of the hollow needle may be located in the instrument tip and does not protrude through the opening; and when the hollow needle is in the exposed position, the distal end of the hollow needle may protrude through the opening. In this manner, the hollow needle may be protected inside the instrument tip when it is in the retracted position.

In some embodiments, the hollow needle may, when in the exposed position, be electrically connected to the outer conductor at a position on the hollow needle that corresponds to an integer number of half wavelengths of the microwave energy away from a distal end of the hollow needle. For example, the grounding element may be located half a wavelength away from the distal end of the hollow needle. This may ensure that, at microwave frequencies, the distal end of the needle is at the same voltage as the part of the needle that is grounded to the outer conductor. This may reduce interference caused by the hollow needle. Where the needle is movable relative to the instrument tip, the retracted position and the exposed positions may be set such that, in each position, the distal end of the hollow needle is an integer number of wavelengths away from the position at which it is grounded. This may minimise interference caused by the hollow needle when it is in the retracted and exposed positions.

In some embodiments, the instrument tip may further comprise a dielectric body, and the energy delivery structure (i.e. the radiating structure) may be formed in and/or on the dielectric body. The dielectric body may be made of any suitable dielectric (insulating) material. The material of the dielectric body may be selected to improve impedance matching with target tissue, in order to improve the efficiency with which EM energy is delivered to target tissue. In some cases, the dielectric body may include multiple different pieces of dielectric material, which are selected and arranged to shape the radiation profile in a desired manner. The dielectric body may act as a support of the radiating structure, e.g. portions of the radiating structure may be formed on or within the dielectric body.

The dielectric body may be a cylinder having a longitudinal axis aligned with the coaxial cable, and wherein the dielectric body comprises a longitudinally extending channel formed therein, and a portion of the hollow needle is received in the longitudinally extending channel. The channel in the dielectric body may serve to maintain a position of the hollow needle in the instrument tip. In this manner, the channel in the dielectric body may restrict or prevent lateral movement of the hollow needle. This may enable accurate positioning of the hollow needle, to facilitate insertion of the hollow needle into target tissue. The channel in the dielectric body may be open, e.g. it may be formed by a groove on a surface of the dielectric body, or it may be closed, e.g. it may be formed by a tunnel (passageway) through a portion of the dielectric body. Where the channel is open, it may be formed between two ridges in the dielectric body. Where the instrument includes a second insulating sleeve, the second insulating sleeve may extend within the channel in the dielectric body, to isolate the hollow needle from the radiating structure.

The opening at the distal end of the instrument tip may be formed at a distal end of the channel in the dielectric body.

In some embodiments, the radiating structure may include a first electrode that is electrically connected to the inner conductor, and a second electrode that is electrically connected to the outer conductor, the first electrode and the second electrode being exposed on a surface of the dielectric body. The first and second electrodes may act as bipolar RF electrodes, e.g. they may act as active and return electrodes, respectively, when RF energy is conveyed to the instrument tip. In this manner, biological tissue that is located in a region around the first and second electrodes may be ablated and/or coagulated with the RF energy. The first and second electrodes may be arranged on the surface of the dielectric body in order to obtain a desired treatment profile. The first electrode may be electrically connected to the inner conductor via an intermediate conductor which extends through a portion of the dielectric body.

The first and second electrodes may be configured to enable treatment of tissue with RF and/or microwave frequencies. For example, when RF energy is conveyed to the instrument tip, the first and second electrodes may act as bipolar RF electrodes. When microwave energy is conveyed to the instrument tip, the first and second electrodes may act as a bipolar microwave antenna. Advantageously, this may enable a user to rapidly switch between treatment modalities (e.g. RF coagulation and microwave ablation), without having to change electrosurgical instruments during a surgical procedure.

In some embodiments, the second electrode may be electrically connected to the outer conductor via the grounding element. In this manner, both the hollow needle and the second electrode may be electrically connected to the outer conductor via the grounding element. As a result, only a single electrical connection may need to be made to the outer conductor, i.e. the one between the outer conductor and the grounding element. This may facilitate electrically connecting the second electrode to the outer conductor.

In some embodiments, the dielectric body may include a first groove in which the first electrode is disposed and a second groove in which the second electrode is disposed. A thickness of dielectric material of the dielectric body may be disposed between the first groove and the second groove, so that the first and second electrodes are isolated by the thickness of dielectric material. A thickness of the first electrode may correspond to a depth of the first groove, so that the first electrode lies flush with an outer surface of the dielectric body. Similarly, a thickness of the second electrode may correspond to a depth of the second groove, so that the second electrode lies flush with the outer surface of the dielectric body. This may provide a smooth outer surface to the instrument tip. This may avoid any sharp edges on the instrument tip, which could catch on tissue. A groove may be an indentation or a depression in an outer surface of the dielectric body. In some cases, a groove may be formed between two or more portions of the dielectric body.

In some embodiments, the first electrode may include a first set of longitudinally extending conductive fingers arranged circumferentially around the dielectric body. A conductive finger of the first electrode may be an elongate conductive element which is oriented along the longitudinal direction. All of the first set of conductive fingers may be electrically connected together to form the first electrode. The first set of conductive fingers may be substantially parallel and arranged around a circumference of the dielectric body, e.g. each of the conductive fingers may be at a different position around the circumference of the dielectric body. For example, where the dielectric body is cylindrical, the conductive fingers may be parallel to axis of the cylindrical body and disposed at different positions on the side of the cylindrical body. Having multiple conductive fingers arranged around the circumference of the dielectric body may enable biological tissue to be treated in multiple directions around the instrument tip. The first set of conductive fingers may be evenly spaced around the circumference of the dielectric body. This may improve the axial symmetry of the radiation profile of the instrument tip, and enable substantially uniform treatment of tissue disposed around the instrument tip. The conductive fingers of the first electrode may be located in a first set of grooves in the dielectric body.

In some embodiments, the second electrode may include a second set of longitudinally extending conductive fingers arranged circumferentially around the dielectric body, and the first set and second set of conductive fingers may be alternatingly arranged around a circumference of the dielectric body. A conductive finger of the second electrode may be an elongate conductive element which is oriented along the longitudinal direction. All of the second set of conductive fingers may be electrically connected together to form the first electrode. The second set of conductive fingers may be substantially parallel and arranged around a circumference of the dielectric body, e.g. each of the conductive fingers may be at a different position around the circumference of the dielectric body. The conductive fingers of the second electrode may be located in a second set of grooves in the dielectric body. The first set of grooves and the second set of grooves may be separated by portions of the dielectric body, so that the conductive fingers of the first electrode and the second electrode are electrically isolated from each other by the dielectric body.

The first and second set of conductive fingers may be alternatingly arranged around the circumference of the dielectric body, e.g. the conductive fingers may be ordered to alternate between the first set and the second set around the circumference. In this manner, each conductive finger in the first set may be located between two conductive fingers in the second set (and vice versa). The first and second electrodes may thus be interdigitated electrodes. This configuration may serve to provide a substantially uniform radiation profile around the instrument tip. This may enable, for example, tissue to be uniformly ablated or coagulated in a volume around the instrument tip.

In some embodiments, the instrument tip may further comprise an annular conductor electrically connected to the outer conductor, the annular conductor forming a portion of an outer surface of the electrosurgical instrument and shielding an electrical connection between the coaxial feed cable and the radiating structure. The annular conductor may be a hollow cylindrical piece of conductive material. The annular conductor may be disposed near a proximal end of the instrument tip, around a junction between the coaxial feed cable and the radiating structure. The electrical connection between the coaxial feed cable and the radiating structure may include an electrical connection between the inner conductor and a conductive element of the radiating structure (e.g. the elongate conductor). Such an electrical connection may involve a length of unshielded wire between the inner conductor and the radiating structure. Such a length of unshielded wire may be susceptible to electrical interference. As the annular conductor is electrically connected to the outer conductor, it may serve to shield any wiring or electrical connections located inside the annular conductor from electrical interference. The annular conductor may therefore reduce interference at the junction between the coaxial feed cable and radiating structure, to improve performance of the instrument tip. The annular conductor may also serve to physically protect the connection between the coaxial feed cable and the radiating structure, by providing a barrier around the connection. The annular conductor may be electrically connected to the outer conductor via the grounding element.

In some cases, the annular conductor may constitute a return electrode for RF energy. Where the instrument tip includes first and second electrodes on the surface of the dielectric body, the annular conductor may constitute an extension of the second electrode. This may serve to increase an effective area of the second electrode. In some cases, the annular conductor may be a proximal portion of the second electrode.

In some embodiments, a distal end of the instrument tip may be shaped in a smoothly contoured manner to be suitable for applying a pressure spot to a target area. For example, the distal end of the instrument tip may be rounded and/or smoothly tapered. This may enable the instrument tip to be pressed against a target area to stem bleeding (e.g. haemostasis). EM energy may then be delivered by the instrument tip, in order to coagulate tissue and stop or control the bleeding.

The electrosurgical instrument discussed above may form part of a complete electrosurgical system. For example, the system may include an electrosurgical generator arranged to supply microwave energy and radiofrequency energy; and the electrosurgical instrument of the invention connected to receive the microwave energy and radiofrequency energy from the electrosurgical generator. The electrosurgical apparatus may further include a surgical scoping device (e.g. an endoscope) having a flexible insertion cord for insertion into a patient's body, wherein the flexible insertion cord has an instrument channel running along its length, and wherein the electrosurgical instrument is dimensioned to fit within the instrument channel.

In this specification "microwave" may be used broadly to indicate a frequency range of 400 MHz to 100 GHz, but preferably the range 1 GHz to 60 GHz. Preferred spot frequencies for microwave EM energy include: 915 MHz, 2.45 GHz, 3.3 GHz, 5.8 GHz, 10 GHz, 14.5 GHz and 24 GHz. 5.8 GHz may be preferred. In contrast, this specification uses "radiofrequency" or "RF" to indicate a frequency range that is at least three orders of magnitude lower, e.g. up to 300 MHz. Preferably, RF energy has a frequency that is high enough to prevent nerve stimulation (e.g. greater than 10 kHz), and low enough to prevent tissue blanching or thermal spread (e.g. lower than 10 MHz). A preferred frequency range for RF energy may be between 100 kHz and 1 MHz.

Herein, the terms "proximal" and "distal" refer to the ends of the electrosurgical instrument further from and closer to the treatment site, respectively. Thus, in use, the proximal end of the electrosurgical instrument is closer to a generator for providing the RF and/or microwave energy, whereas the distal end is closer to the treatment site, i.e. target tissue in the patient.

The term "conductive" is used herein to mean electrically conductive, unless the context dictates otherwise.

The term "longitudinal" used below refers to the direction along the length of the electrosurgical instrument, parallel to the axis of the coaxial transmission line. The term "inner" means radially closer to the centre (e.g. axis) of the instrument. The term "outer" means radially further from the centre (axis) of the instrument.

The term "electrosurgical" is used in relation an instrument, apparatus or tool which is used during surgery and which utilises microwave and/or radiofrequency electromagnetic (EM) energy.

BRIEF DESCRIPTION OF THE DRAWINGS

Embodiments of the invention will now be described by way of example with reference to the accompanying drawings in which:

FIG. 10b shows a perspective view of the dielectric body of FIG. 10a.

DETAILED DESCRIPTION; FURTHER OPTIONS AND PREFERENCES

Figure 1:
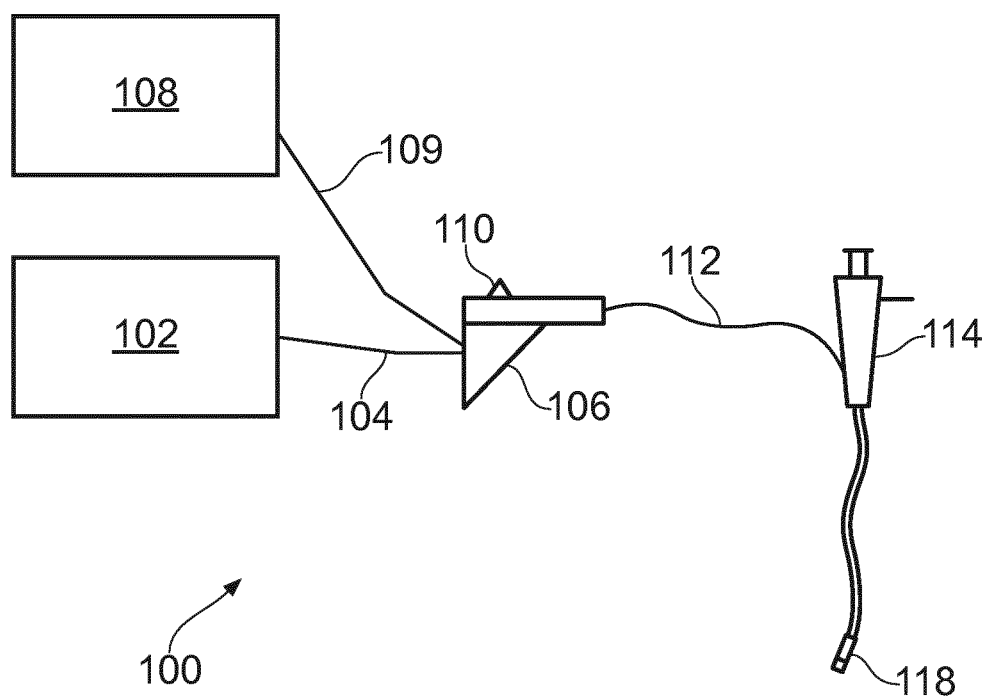
FIG. 1 is a schematic diagram of an electrosurgical system that is an embodiment of the invention.

FIG. 1 is a schematic diagram of a complete electrosurgical system 100 that is capable of supplying microwave energy and radiofrequency energy to the distal end of an invasive electrosurgical instrument. The system 100 comprises a generator 102 for controllably supplying microwave and radiofrequency energy. A suitable generator for this purpose is described in WO 2012/076844, which is incorporated herein by reference. The generator may be arranged to monitor reflected signals received back from the instrument in order to determine an appropriate power level for delivery. For example, the generator may be arranged to calculate an impedance seen at the distal end of the instrument in order to determine an optimal delivery power level. The generator 102 is connected to an interface joint 106 by an interface cable 104.

The system 100 also includes a fluid supply unit 108, which contains a fluid for use with the electrosurgical instrument. The fluid may be a liquid (e.g. liquid medication) or gas (e.g. argon gas). The fluid supply unit 108 is fluidly connected to the interface joint 106 via a fluid conduit 109. The fluid supply unit 108 may dispense fluid contained therein via the fluid conduit 109. For example, the fluid supply unit 108 may include a syringe for dispensing liquid medication.

The interface joint 106 houses an instrument control mechanism that is operable by sliding a trigger 110, e.g. to control longitudinal (back and forth) movement of one or more control wires or push rods (not shown). If there is a plurality of control wires, there may be multiple sliding triggers on the interface joint to provide full control. The function of the interface joint 106 is to combine the inputs from the generator 102, the fluid supply unit 108 and the instrument control mechanism into a single flexible shaft 112, which extends from the distal end of the interface joint 106. In other embodiments, other types of input may also be connected to the interface joint 106.

The flexible shaft 112 is insertable through the entire length of an instrument (working) channel of an endoscope 114. The flexible shaft 112 has a distal assembly 118 (not drawn to scale in FIG. 1) that is shaped to pass through the instrument channel of the endoscope 114 and protrude (e.g. inside the patient) at the distal end of the endoscope's instrument channel. The distal end assembly 118 includes an instrument tip for delivering microwave energy and radiofrequency energy into biological tissue. The tip is also configured to deliver fluid from the fluid supply unit 108. The tip configuration is discussed in more detail below.

The structure of the distal assembly 118 may be arranged to have a maximum outer diameter suitable for passing through the working channel. Typically, the diameter of a working channel in a surgical scoping device such as an endoscope is less than 4.0 mm, e.g. any one of 2.8 mm, 3.2 mm, 3.7 mm, 3.8 mm. The length of the flexible shaft 112 can be equal to or greater than 0.3 m, e.g. 2 m or more. In other examples, the distal assembly 118 may be mounted at the distal end of the flexible shaft 112 after the shaft has been inserted through the working channel (and before the instrument cord is introduced into the patient). Alternatively, the flexible shaft 112 can be inserted into the working channel from the distal end before making its proximal connections. In these arrangements, the distal end assembly 118 can be permitted to have dimensions greater than the working channel of the surgical scoping device 114.

The system described above is one way of introducing the instrument into a patient's body. Other techniques are possible. For example, the instrument may also be inserted using a catheter.

Figure 2:
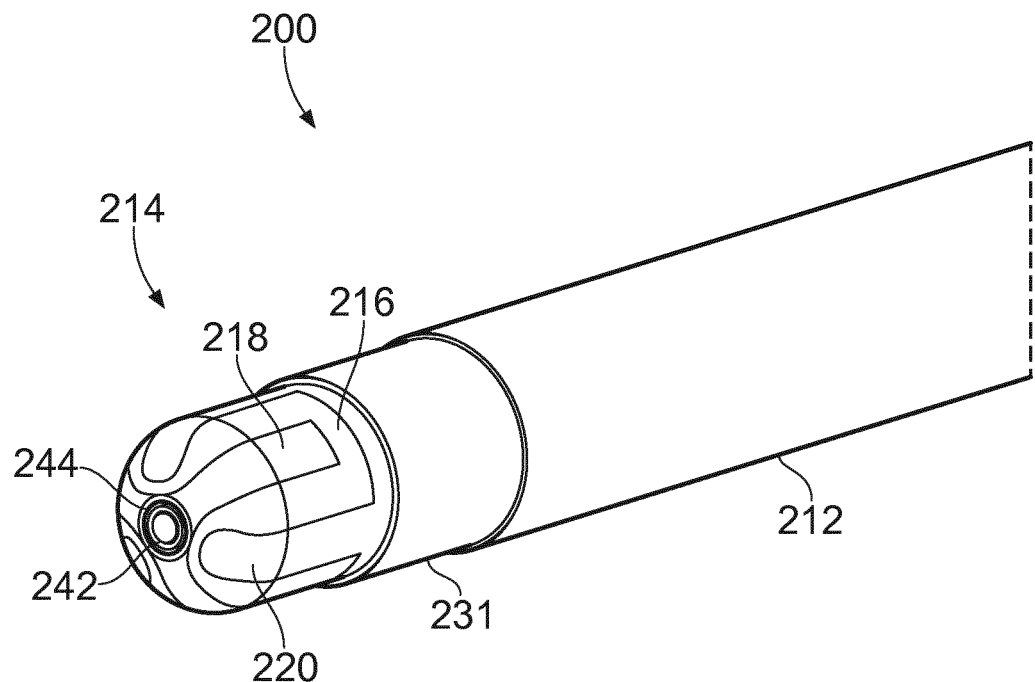
FIG. 2 is a perspective view of an electrosurgical instrument that is an embodiment of the invention, where a hollow needle of the instrument is in a retracted position.
Figure 3:
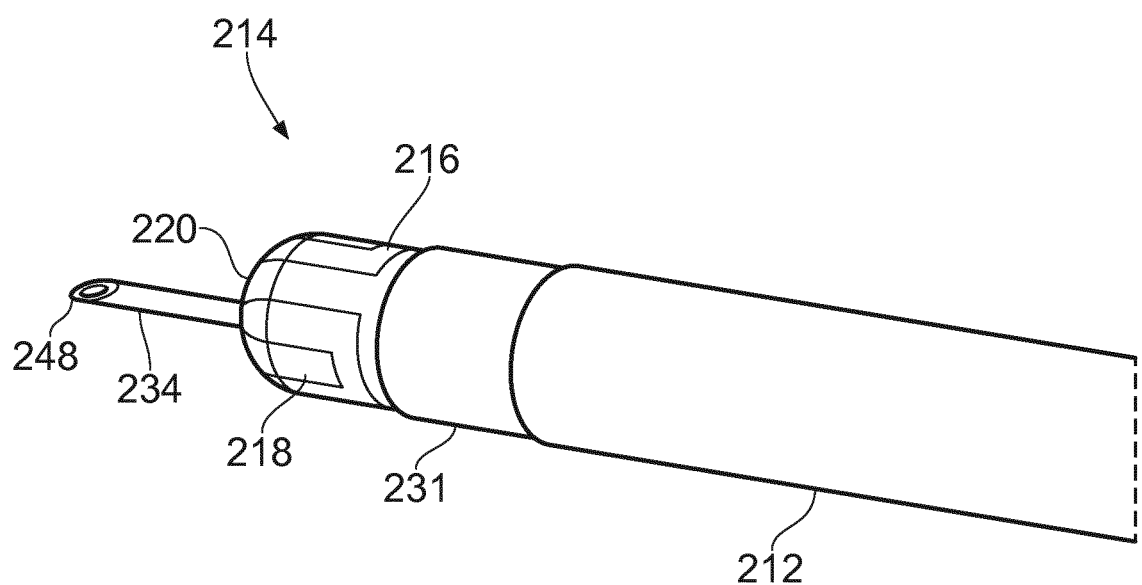
FIG. 3 is a perspective view of the electrosurgical instrument of FIG. 2, where the hollow needle is in an exposed position.
Figure 4:
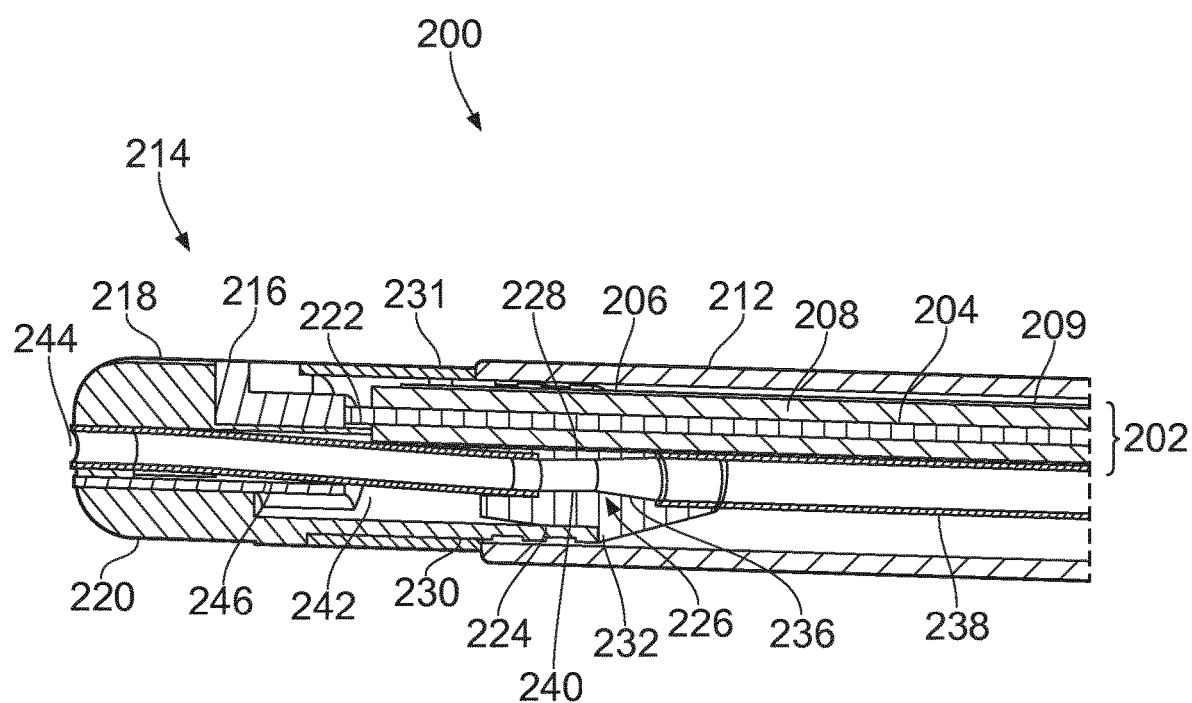
FIG. 4 is a schematic cross-sectional view the electrosurgical instrument of FIG. 2.
Figure 5:
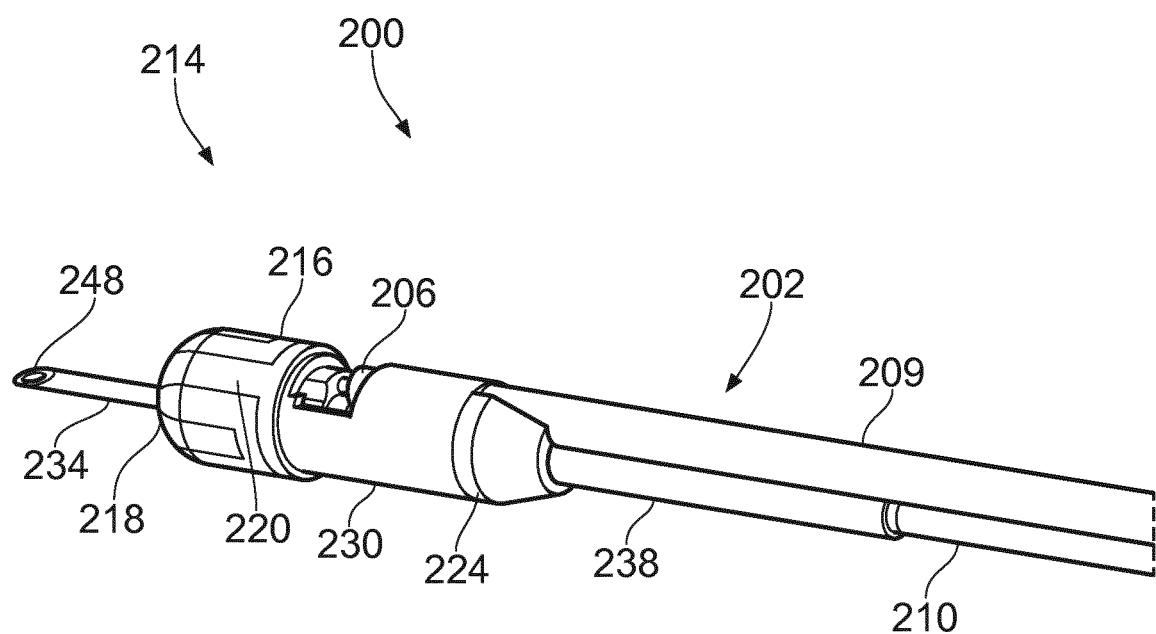
FIG. 5 is a perspective view of the electrosurgical instrument of FIG. 2, where a flexible instrument sleeve of the instrument has been omitted, to reveal an internal structure of the instrument.

FIG. 2 shows a perspective view of a distal end of an electrosurgical instrument 200 that is an embodiment of the invention. The distal end of the electrosurgical instrument 200 may correspond, for example, to the distal assembly 118 discussed above. FIG. 3 shows another perspective view of the electrosurgical instrument 200. FIG. 4 shows a cross-sectional side view of the electrosurgical instrument 200. FIG. 5 shows a perspective view of the electrosurgical instrument 200, where a flexible instrument sleeve of the instrument has been omitted, to reveal an internal structure of the instrument.

The electrosurgical instrument 200 includes a coaxial feed cable 202 that is connectable at its proximal end to a generator (such as generator 102) in order to convey microwave energy and RF energy. The coaxial feed cable 202 comprises an inner conductor 204 and an outer conductor 206 which are separated by a dielectric material 208. The coaxial feed cable 202 is preferably low loss for microwave energy. A choke (not shown) may be provided on the coaxial feed cable 204 to inhibit back propagation of microwave energy reflected from the distal end and therefore limit backward heating along the device. An insulating coating 209 is provided on an outer surface of the outer conductor 206, to insulate and protect the coaxial feed cable 202.

The electrosurgical instrument 200 further includes a fluid channel 210 which extends alongside the coaxial feed cable 202. The fluid channel 210 may serve to convey fluid from a proximal end of the instrument to the distal end of the instrument. For example, the proximal end of the fluid channel 210 may be connectable to fluid supply unit 108. Both the coaxial feed cable 202 and the fluid channel 210 are housed within a flexible instrument sleeve 212. The flexible instrument sleeve 212 may be made of or coated with a biocompatible non-stick material (e.g. PTFE), to prevent tissue from sticking to it.

The electrosurgical instrument 200 includes an instrument tip 214 which is located at a distal end of the coaxial feed cable 202. The instrument tip 214 includes a dielectric body 216 made of an insulating material (e.g. PEEK). The dielectric body 216 has a radiating structure formed on an outer surface thereof, the radiating structure including an inner electrode 218 and an outer electrode 220. The inner electrode 218 is electrically connected to the inner conductor 204 of the coaxial feed cable 202 via an electrical connection 222 (see FIG. 4). The structure of the inner conductor 204 is discussed in more detail below with reference to FIGS. 10a and 10b, which show the dielectric body 216 in isolation. The electrical connection 222 may for example be a soldered or welded electrical connection, or it may be formed using a conductive adhesive (e.g. conductive epoxy). The electrical connection 222 between the inner conductor 204 and the inner electrode 218 may be potted, e.g. it may be encased in a solid or gelatinous compound for protection.

Figure 9A:
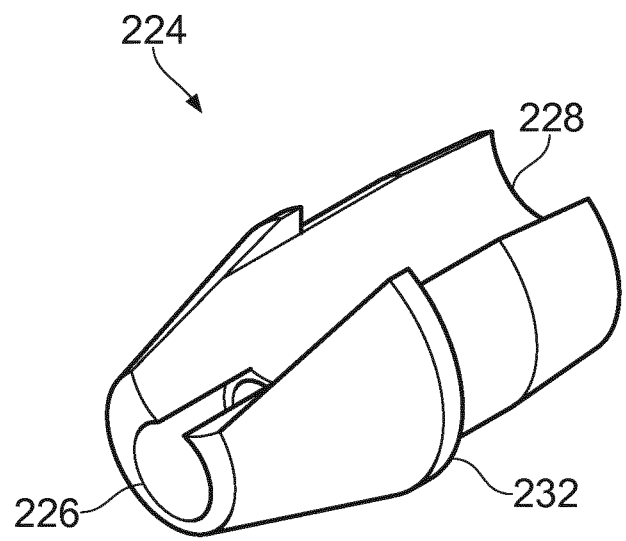
FIGS. 9a and 9b are perspective views of a grounding element that may be used in an electrosurgical instrument that is an embodiment of the invention.
Figure 9B:
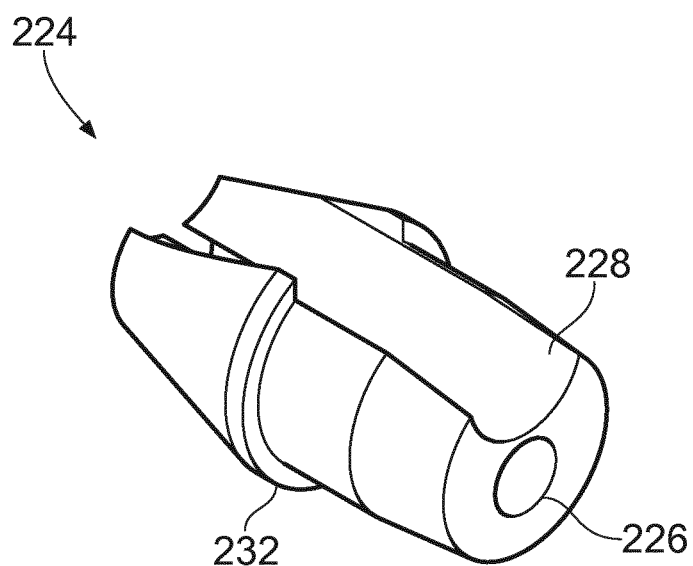

The instrument tip 214 further includes a grounding element 224 located near a proximal end of the instrument tip 214. The grounding element 224 is made of a conductive material (e.g. metal), and may be formed as a unitary component. The structure of the grounding element 224 is illustrated in more detail in FIGS. 9a and 9b, which show perspective views of the grounding element 224. A first channel 226 and a second channel 228 which extend in the longitudinal direction are formed in the grounding element 224. The first channel 226 is a closed channel, and is configured to receive a hollow needle as described below. The second channel 228 is an open channel, i.e. it is formed by a groove on an outer surface of the grounding element 224. A distal portion of the coaxial feed cable 202 is held in the second channel 228 of the grounding element 224. The shape of the second channel 228 is complementary to the shape of the distal portion of the coaxial feed cable 202. The second channel 229 may be shaped to retain (e.g. by interference fit) the coaxial feed cable 202. In some cases, the outer conductor 206 may be secured to the grounding element 224, e.g. using conductive epoxy.

The insulating coating 209 is stripped away from the distal portion of the coaxial cable 202 that is held in the second channel 228 of the grounding element 224. In this manner, the outer conductor 206 in the distal portion of the coaxial feed cable 202 is exposed and is in electrical contact with a surface of the second channel 228 of the grounding element 224. In this manner, the outer conductor 206 is electrically connected to the grounding element 224.

The second electrode 220 includes a proximal portion 230 which extends towards a proximal end of the instrument tip 214. The proximal portion 230 is formed by a cylindrical hollow conductor, which is disposed around the grounding element 224 and the distal portion of the coaxial feed cable 202. The proximal portion 230 is in electrical contact with an outer surface of the grounding element 224 and an exposed portion of the outer conductor 206. In this manner, the second electrode 220 is electrically connected to the outer conductor 206. The proximal portion 230 of the second electrode 220 may serve to hold the outer conductor 206 against the grounding element 224, to ensure that the electrical connection between the grounding element 224 and the outer conductor 206 is maintained. The grounding element 224 includes a lip 232 against which the proximal portion 230 of the second electrode 220 abuts. This may serve to maintain the relative positions of the grounding element and the proximal portion 230. The proximal portion 230 of the outer electrode 220 may be soldered to the outer conductor 206 and/or the grounding element, or it may be secured using other means (e.g. conductive epoxy).

The instrument tip further includes an outer annular conductor 231, which is disposed around the proximal portion 230 of the outer electrode 220. The annular conductor 231 is a hollow cylindrical piece of conductive material. The annular conductor 231 is electrically connected to the proximal portion 230 of the outer electrode 220. The annular conductor 231 is arranged to shield the electrical connection 222 between the inner conductor 204 and the inner electrode 218. The annular conductor 231 may thus protect the electrical connection 222 from electrical interference, as well as protect the electrical connection from physical damage.

A needle passageway is formed in the instrument tip 214 for receiving a hollow needle 234 that is in fluid communication with the fluid channel 210. The hollow needle 234 is movable relative to the instrument tip 214 through the needle passageway, as discussed below in relation to FIGS. 6-8. For illustration purposes, the hollow needle 234 is omitted from FIG. 4.

The needle passageway is formed by multiple components in the instrument tip 214. At its proximal end, the needle passageway is formed by the first channel 226 in the grounding element 224. The first channel 226 includes a flared portion 236 at a proximal end. The flared portion 236 flares outwards, i.e. a cross-sectional area of the flared portion 236 increases towards the proximal end of the first channel 226. The flared portion 236 may serve to guide (e.g. deflect or funnel) the hollow needle 234 into the first channel 226. A first insulating sleeve 238 extends from the first channel 226 in a proximal direction towards the fluid channel 210. The first insulating sleeve 238 may serve to guide the hollow needle 234 towards the grounding element 224 and into the first channel 226. The first channel 226 further includes contact portion 240. The contact portion 238 of the first channel 226 has a cross-section that substantially matches a cross-section of the hollow needle 234, i.e. the shape of the contact portion 238 may be complementary to shape of the hollow needle 234. In this manner, when the hollow needle 234 extends through the contact portion 240 of the first channel 226, the hollow needle 234 may contact a surface in the first channel 226 (e.g. a wall of the first channel 226), to form an electrical contact between the hollow needle 234 and the grounding element 224. This may serve to short the hollow needle 234 to the outer conductor 206. The outer conductor 206 may typically be grounded (e.g. it may be at 0 V), so the hollow needle 234 may also be grounded when it is in the first channel 226.

The needle passageway further includes a second insulating sleeve 242 which extends from a distal end of the first channel 226. The second insulating sleeve 242 extends through the distal tip 214 to an opening 244 at a distal end of the distal tip 214. The second insulating sleeve 242 passes through a channel 246 in the dielectric body 216. The second insulating sleeve 242 serves to electrically isolate the hollow needle 234 from the inner electrode 218.

A cross-section of the second insulating sleeve 242 is smaller than a cross-section of the first insulating sleeve 238. The cross-section of the second insulating sleeve 238 is be approximately the same size as the cross-section of the of the contact portion 238 of the first channel 226. This may serve to ensure accurate positioning of the hollow needle 234 when it is moved through the instrument tip 214. By using a larger cross-section for the first insulating sleeve 238 compared with the second insulating sleeve 242, resistance to movement of the hollow needle 234 along the needle passageway (e.g. due to friction between the hollow needle 234 and the insulating sleeves) may be reduced. This may facilitate moving the hollow needle 234 relative to the instrument tip 214.

The hollow needle 234 is in fluid communication with the fluid channel 210. The hollow needle 234 extends from a distal end of the fluid channel towards the instrument tip 214. A distal tip 248 of the hollow needle 234 is pointed, to facilitate insertion of the hollow needle 234 into tissue. The hollow needle 234 may be a hollow tube of material suitable for injecting fluid into tissue, e.g. stainless steel. For example, the hollow needle 234 may be a hypodermic needle. A proximal portion of the hollow needle 234 is received in a distal portion of the fluid channel 210, so that fluid conveyed by the fluid channel 210 may flow into the hollow needle 234. A seal may be formed between the fluid channel 210 and the hollow needle 234, to prevent fluid from leaking.

Figure 6:
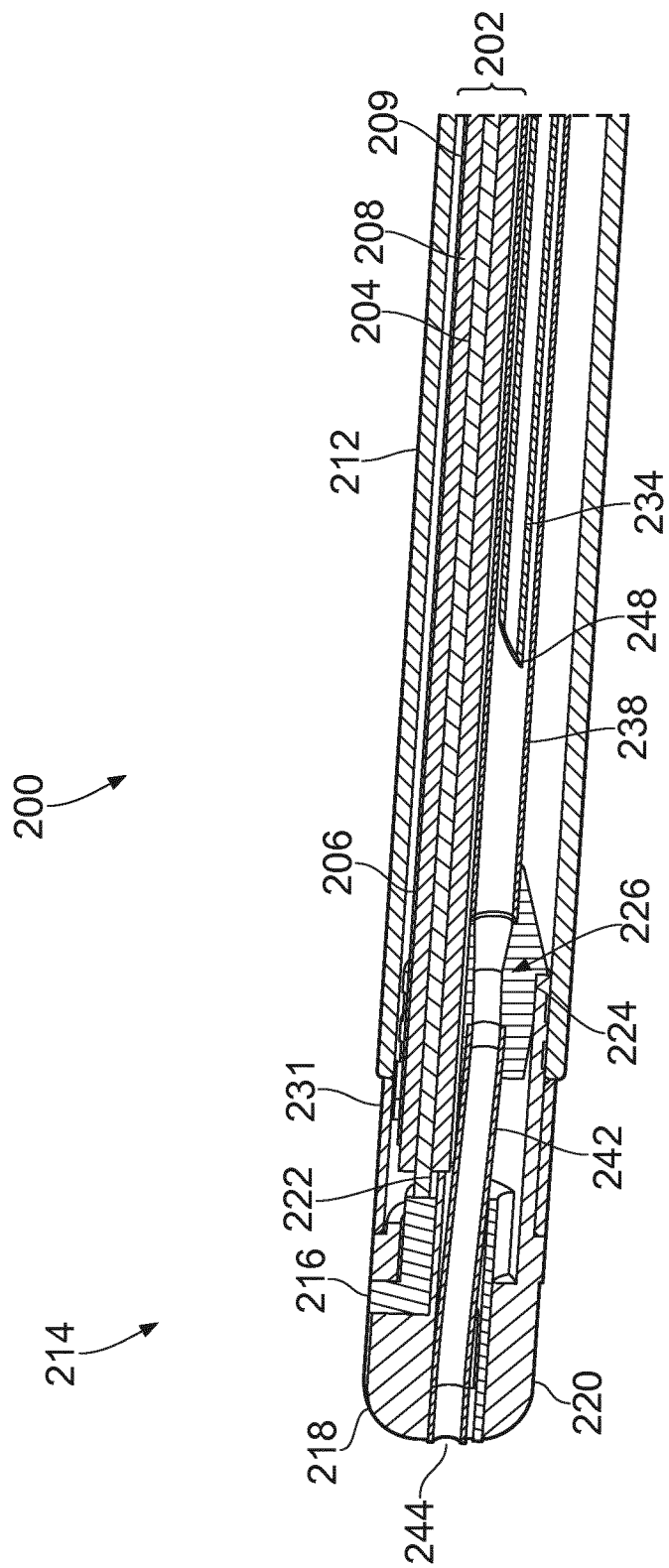
FIGS. 6-8 are schematic cross-sectional views of the electrosurgical instrument of FIG. 2 showing the hollow needle in different positions.
Figure 7:
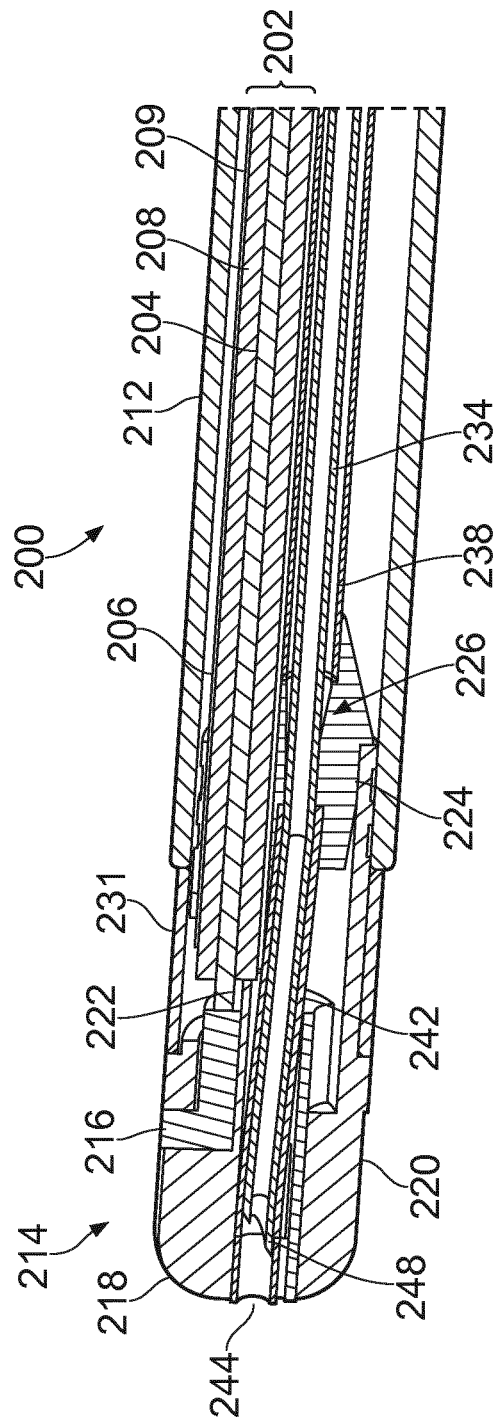
Figure 8:
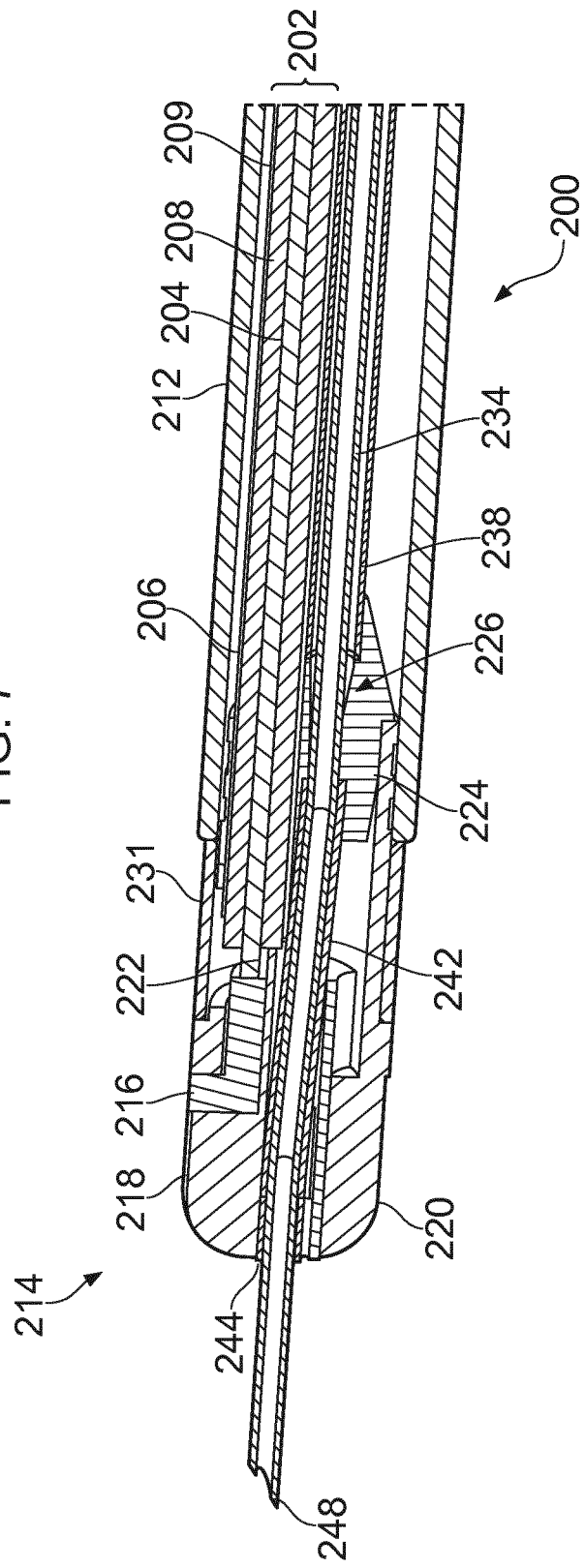

FIGS. 6 to 8 show cross-sectional side views of electrosurgical instrument 200, where the hollow needle 234 is in different positions. In FIG. 6, the hollow needle is in a first retracted position, such that its distal tip 248 is located inside the first insulating sleeve 238. In FIG. 7, the hollow needle 234 is in a second retracted position, where its distal tip 248 is located inside the second insulating second insulating sleeve 242, so that it does not protrude through the opening 244 in the distal tip 214. In FIG. 8, the hollow needle 234 is in an exposed position, where its distal tip 248 protrudes through the opening 244 and a distal portion of the hollow needle 234 extends beyond the instrument tip 214.

The hollow needle 234 may be movable between the positions illustrated in FIGS. 6-8 via any suitable means. For example, the hollow needle 234 may be movable using a control wire (not shown) that extends through the fluid channel 210 to a proximal end of the instrument 200.

When the hollow needle 234 is in the first retracted position (FIG. 6), the hollow needle is fully retracted from the instrument tip 214, i.e. it is not located in the instrument tip 214. In this configuration, the hollow needle 234 is not electrically connected to the outer conductor 206. As the hollow needle 234 is fully retracted from the instrument tip 214, the hollow needle 234 does not interfere with microwave energy emitted at the instrument tip (i.e. via the inner and outer electrodes 218, 220).

When the hollow needle 234 is in the second retracted position (FIG. 7), the distal tip 248 of the hollow needle 234 is located in the instrument tip 214. In this configuration, a portion of the hollow needle 234 is received inside the contact portion 240 of the first channel 226 of the grounding element 224. In this manner, the hollow needle 234 is electrically connected to the grounding element 224 in the contact portion 240. As a result, the hollow needle 234 is electrically connected to the outer conductor 206 of the coaxial feed cable 202 via the grounding element 224. This may reduce or prevent interference of the hollow needle 234 with EM energy radiated by the instrument tip 214 (i.e. via the inner and outer electrodes 218, 220).

When the hollow needle 234 is in the exposed position (FIG. 8), the hollow needle 234 protrudes through the opening 244 in the instrument tip 214. In this configuration, the hollow needle 234 may be used to dispense fluid from the fluid conduit 210 into a treatment site. For example, the pointed distal tip 248 of the hollow needle 234 may be inserted into target tissue, to inject liquid medicine into the target tissue. Similarly to the second retracted position, a portion of the hollow needle 234 is received in the contact portion 240 of the first channel 226 of the grounding element 224. As a result, the hollow needle 234 is electrically connected to the outer conductor 206 of the coaxial feed cable 202 via the grounding element 224, which may reduce interference caused by the hollow needle 234. Therefore, regardless of whether the hollow needle 234 is in the first retracted position, the second retracted position or the exposed position, interference of the hollow needle 234 with radiated EM energy may be avoided.

The electrical contact formed between the hollow needle 234 and the contact portion 240 of the first channel 226 may thus be at a sliding interface between the needle and the grounding element, i.e. it enables the hollow needle 234 to be moved through the first channel 226 whilst maintaining electrical contact between the hollow needle 234 and the grounding element 224.

The grounding element 224 may be located in the instrument tip 214 such that it is an integer number of half wavelengths (of the conveyed microwave energy) away from the distal tip 248 of the hollow needle 234 when the hollow needle is in the second retracted position and/or the exposed position. This may ensure that at microwave frequencies the distal tip 248 of the hollow needle 234 and the part of the hollow needle 234 in the first channel 226 are at the same voltage (i.e. that of the outer conductor 206). For example, for a microwave energy frequency of 5.8 GHz, a quarter wavelength of the microwave energy may be approximately 12.9 mm (assuming the waveguide is unloaded). If the hollow needle 234 is shorted to ground (e.g. 0 V) 2×12.9 mm away from its distal tip 248, then the distal tip 248 may also be shorted to ground. So, in this example, the grounding element 224 may be placed approximately 2×12.9 mm=25.8 mm away from the distal tip 248 of the hollow needle 234 when the hollow needle 234 is in the exposed position. The distance of travel of the needle may be set so that the electric connection to the grounding element 224 is a multiple of half wavelengths of the microwave energy from the distal tip in both the retracted and exposed positions.

Figure 10A:
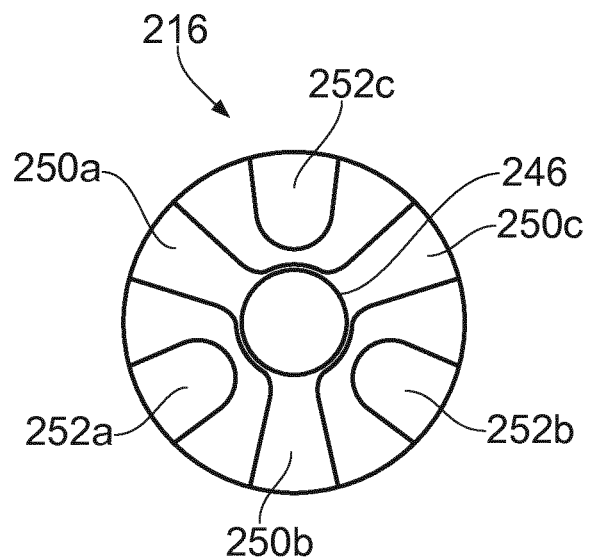
FIG. 10a shows a front view of a dielectric body that may be used in an electrosurgical instrument that is an embodiment of the invention.
Figure 10B:
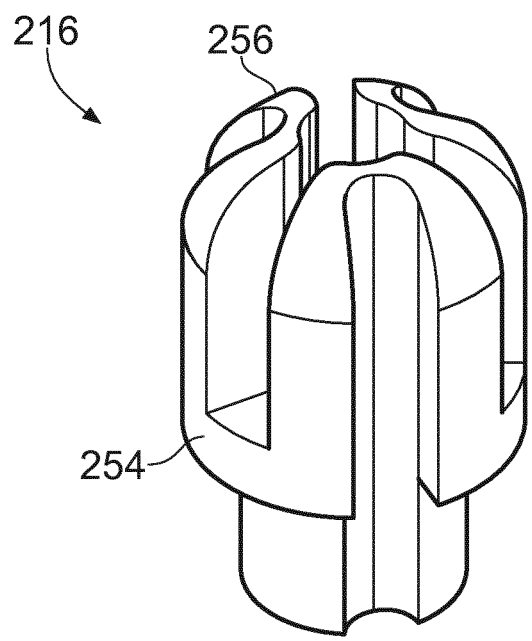

FIG. 10a shows a front view of the dielectric body 216 of the instrument tip 214. FIG. 10b shows a perspective view of the dielectric body 216 of the instrument tip 214. The dielectric body 216 is formed of a unitary piece of insulating material (e.g. PEEK). The dielectric body 216 includes a first set of grooves 250a, 250b, 250c in which the inner electrode 218 is formed, and a second set of grooves 252a, 252b, 252c in which the outer electrode 220 is formed. The first set of grooves 250a-c and the second set of grooves 252a-c are formed in an outer surface 254 of the dielectric body 216, and extend in the longitudinal direction. In the example shown, both the first set of grooves 250a-c and the second set of grooves 252a-c include three grooves. In other examples, different numbers of grooves may be used. The grooves in the first set and the second set are alternatingly arranged around a circumference of the dielectric body 216. Thus, each groove of the first set 250a-c is located between two grooves in the second set 252a-c. Adjacent grooves in the dielectric body 216 are separated by a portion of the dielectric body 216. The outer surface 254 of the dielectric body 216 has a generally cylindrical shape, and forms part of an outer surface of the instrument tip 214. A distal end 256 of the dielectric body 216 is rounded, e.g. shaped in a smoothly contoured manner.

The inner electrode 218 is formed by a unitary piece of conductive material (e.g. metal) having three longitudinally extending conductive fingers 258a, 258b, 258c. Each of the conductive fingers 258a-c is located in a respective one of the first set of grooves 250a-c in the dielectric body 216. The outer electrode 220 is formed by a unitary piece of conductive material (e.g. metal) having three longitudinally extending conductive fingers 260a, 260b, 260c. Each of the conductive fingers 260a-c is located in a respective one of the second set of grooves 252a-c in the dielectric body 216. The conductive fingers 258a-c of the inner electrode 218 are electrically isolated from the conductive fingers 260a-c of the outer electrode 220 by the dielectric body 216. Each conductive finger of the inner electrode 218 is located between two conductive fingers of the outer electrode (and vice versa). In this manner, the inner electrode 218 and outer electrode 220 may thus be considered as interdigitated electrodes.

The inner electrode 218 and the outer electrode 220 are formed so that they lie flush with the outer surface 254 and distal end 256 of the dielectric body 216. This provides a smooth outer surface to the instrument tip 214, which may prevent tissue from catching on the instrument tip 214. The instrument tip 214 is coated with a bio-compatible non-stick coating, e.g. made of Parylene C or Parylene D. In this example, the coating has a thickness of around 3 µm, but other thickness may be used, e.g. up to 40 µm. Alternatively or additionally, the inner electrode 218 and outer electrode 220 may be polished to minimise tissue sticking.

The non-stick coating prevents coagulated tissue from sticking to the instrument tip. As a result, damage to tissue may be avoided when the instrument tip 214 is removed from a treatment site following application of EM energy.

The electrosurgical instrument 200 may be particularly suitable for coagulating tissue using microwave energy, in order to stem or control bleeding (haemostasis). The inner electrode 218 and the outer electrode 220 may act as a bipolar microwave antenna when microwave energy is delivered to the instrument tip 214 via the coaxial feed cable 202. In this manner, target tissue located around the instrument tip 214 may be coagulated using microwave energy. The rounded distal end of the instrument tip 214 may make the instrument tip suitable for applying pressure to a treatment area (e.g. a vessel) to act as a tamponade to stem bleeding. Microwave energy may be applied via the instrument tip 214 whilst pressure is applied to the treatment area, to coagulate tissue and stem bleeding.

As the conductive fingers of the inner electrode 218 and the outer electrode 220 are arranged in an alternating order around a circumference of the instrument tip 214, a microwave radiation profile produced by the instrument tip may be substantially uniform around the instrument tip 214. This may enable a substantially uniform treatment of tissue located around the instrument tip 214.

The invention claimed is:

1. An electrosurgical instrument comprising:
a coaxial feed cable for conveying microwave energy, the coaxial feed cable having an inner conductor, an outer conductor, and a dielectric material separating the inner conductor and the outer conductor;
an instrument tip disposed at a distal end of the coaxial feed cable to receive the microwave energy; and
a fluid channel for conveying fluid to the instrument tip, wherein the instrument tip comprises:
a dielectric body;
a radiating structure for radiating the microwave energy into biological tissue, wherein the radiating structure is formed in or on the dielectric body, and wherein the radiating structure includes a first electrode that is electrically connected to the inner conductor, and a second electrode that is electrically connected to the outer conductor, the first electrode and the second electrode being exposed on an outer surface of the dielectric body;
a hollow needle in fluid communication with the fluid channel, the hollow needle being arranged to deliver fluid from the fluid channel to a treatment site, and
a grounding element arranged to electrically connect the hollow needle to the outer conductor;
wherein the radiating structure is coated with an insulating non-stick material.

2. An electrosurgical instrument according to claim 1, wherein the instrument tip is coated with the insulating non-stick material.

3. An electrosurgical instrument according to claim 1, wherein a coating of the insulating non-stick material over the radiating structure has a thickness equal to or less than 40 µm.

4. An electrosurgical instrument according to claim 3, wherein the thickness is equal to or less than 10 µm.

5. An electrosurgical instrument according to claim 1, wherein the insulating non-stick material is Parylene C or Parylene D.

6. An electrosurgical instrument according to claim 1, wherein the grounding element includes a body having a first connection surface and a second connection surface arranged to retain the hollow needle and outer conductor respectively, wherein the first connection surface and the second connection surface are electrically connected together, and wherein the hollow needle is electrically connected to the first connection surface and the outer conductor is electrically connected to the second connection surface.

7. An electrosurgical instrument according to claim 6, wherein:
the body of the grounding element has a first channel extending therethrough, the first connection surface being formed within the first channel;
a portion of the hollow needle is received in the first channel; and
the first channel includes a flared portion located at a proximal end of the first channel, the flared portion having a cross-sectional area that increases towards the proximal end of the first channel.

8. An electrosurgical instrument according to claim 7, wherein:
the body of the grounding element includes a second channel extending therethrough, the second connection surface being formed in the second channel; and
a distal portion of the outer conductor is received in the second channel.

9. An electrosurgical instrument according to claim 6, further comprising:
a first insulating sleeve arranged at a proximal end of the grounding element to guide the hollow needle into contact with the first connection surface, and
a second insulating sleeve arranged at a distal end of the grounding element to insulate the hollow needle from the radiating structure.

10. An electrosurgical instrument according to claim 1, wherein the hollow needle is movable relative to the instrument tip between:
a retracted position, in which a distal end of the hollow needle is set back from a distal end of instrument tip; and
an exposed position, in which the distal end of the hollow needle protrudes beyond the distal end of the instrument tip.

11. An electrosurgical instrument according to claim 10, wherein the hollow needle is slidable relative to the outer conductor, and the electrical connection between the hollow needle and outer conductor passes across a sliding interface.

12. An electrosurgical instrument according to claim 10, wherein the instrument tip includes an opening at the distal end thereof, and wherein:
when the hollow needle is in the retracted position, the distal end of the hollow needle is located in the instrument tip and does not protrude through the opening;
when the hollow needle is in the exposed position, the distal end of the hollow needle protrudes through the opening.

13. An electrosurgical instrument according to claim 10, wherein, when in the exposed position, the hollow needle is electrically connected to the outer conductor via the grounding element at a position on the hollow needle that corresponds to an integer number of half wavelengths of the microwave energy away from the distal end of the hollow needle.

14. An electrosurgical instrument according to claim 1, wherein the dielectric body includes a first groove in which the first electrode is disposed and a second groove in which the second electrode is disposed.

15. An electrosurgical instrument according to claim 1, wherein the dielectric body is a cylinder having a longitudinal axis aligned with the coaxial cable, and wherein the dielectric body comprises a longitudinally extending channel formed therein, and a portion of the hollow needle is received in the longitudinally extending channel.

16. An electrosurgical instrument according to claim 15, wherein the first electrode includes a first set of longitudinally extending conductive fingers disposed around a circumference of the dielectric body.

17. An electrosurgical instrument according to claim 16, wherein the second electrode includes a second set of longitudinally extending conductive fingers disposed around the circumference of the dielectric body, and wherein the first set and second set of conductive fingers are arranged in an interdigitated manner around the circumference of the dielectric body.

18. An electrosurgical instrument according to claim 1, wherein the instrument tip further comprises a shielding conductor electrically connected to the outer conductor and enclosing an electrical connection between the coaxial feed cable and the radiating structure.

19. An electrosurgical instrument according to claim 1, wherein a distal end of the instrument tip is shaped in a smoothly contoured manner to be suitable for applying a pressure spot to a target area.

20. An electrosurgical system for treating biological tissue, the system comprising:
an electrosurgical generator arranged to supply microwave energy or radiofrequency energy; and
an electrosurgical instrument according to claim 1 connected to receive the microwave energy or radiofrequency energy from the electrosurgical generator.

21. An electrosurgical system according to claim 20 further comprising a surgical scoping device having a flexible insertion cord for insertion into a patient's body, wherein the flexible insertion cord has an instrument channel running along its length, and wherein the electrosurgical instrument is dimensioned to fit within the instrument channel.

22. An electrosurgical instrument comprising:
a coaxial feed cable for conveying microwave energy or radiofrequency energy, the coaxial feed cable having an inner conductor, an outer conductor, and a dielectric material separating the inner conductor and the outer conductor;
an instrument tip disposed at a distal end of the coaxial feed cable to receive the microwave energy or the radiofrequency energy; and
a fluid channel for conveying fluid to the instrument tip;
wherein the instrument tip comprises:
a dielectric body;
an energy delivery structure for delivering the microwave energy or the radiofrequency energy into biological tissue; and
a hollow needle in fluid communication with the fluid channel, the hollow needle being arranged to deliver fluid from the fluid channel to a treatment site,
wherein the energy delivery structure comprises a radiating structure for radiating the microwave energy received from the coaxial feed cable into biological tissue,
wherein the radiating structure is formed in or on the dielectric body, and wherein the radiating structure includes a first electrode that is electrically connected to the inner conductor, and a second electrode that is electrically connected to the outer conductor, the first electrode and the second electrode being exposed on an outer surface of the dielectric body, and
wherein the hollow needle is electrically connected to the outer conductor to ground the hollow needle.

* * * * *